United States Patent [19]

Hammami

[11] Patent Number: 5,152,752
[45] Date of Patent: Oct. 6, 1992

[54] SINGLE-USE HYPODERMIC SYRINGE

[76] Inventor: Alain Hammami, 22, rue Caumartin, 75009 Paris, France

[21] Appl. No.: 814,248

[22] Filed: Dec. 23, 1991

Related U.S. Application Data

[63] Continuation of Ser. No. 613,628, Nov. 20, 1990, abandoned.

[30] Foreign Application Priority Data

Mar. 20, 1990 [FR] France .................. 89 03592

[51] Int. Cl.⁵ ............................................. A61M 5/00
[52] U.S. Cl. ..................................... 604/110; 604/218
[58] Field of Search ............... 604/110, 220, 218, 187

[56] References Cited

U.S. PATENT DOCUMENTS

| | | |
|---|---|---|
| 3,834,387 | 8/1974 | Brown . |
| 4,291,695 | 9/1981 | Bekkering et al. ............ 604/227 X |
| 4,687,467 | 8/1987 | Cygielski ............... 604/110 |
| 4,690,154 | 9/1987 | Woodford et al. ........... 128/765 |
| 4,747,830 | 5/1988 | Gloyer ............... 604/110 |
| 4,775,364 | 10/1988 | Alles ............... 604/110 |
| 4,850,968 | 7/1989 | Romano ............... 604/110 |
| 4,863,427 | 9/1989 | Cocchi ............... 604/110 |
| 4,874,372 | 10/1989 | McArthur et al. ........... 604/110 |

FOREIGN PATENT DOCUMENTS

| | | |
|---|---|---|
| 304386 | 5/1988 | European Pat. Off. ............ 604/110 |
| 0291109 | 11/1988 | European Pat. Off. . |
| 0345159 | 12/1989 | European Pat. Off. . |
| 1039984 | 10/1953 | France . |
| 2412320 | 7/1979 | France . |
| 255256 | 6/1948 | Netherlands . |
| 1150980 | 5/1969 | United Kingdom . |
| 2205750 | 12/1988 | United Kingdom ............ 604/110 |
| 89/03231 | 4/1989 | World Int. Prop. O. ........... 604/110 |

Primary Examiner—John D. Yasko
Attorney, Agent, or Firm—Seidel, Gonda, Lavorgna & Monaco

[57] ABSTRACT a) Single-use hypodermic syringe b) the said syringe being characterized in that: the front closed face (31) of the adaptor (3) comprises a fragile wall (34), the rear face (32) of the adaptor comprises in addition to the orifice (33), at least one other aperture (35) which is situated outside the field of contact of the drive nipple (4) and of the adaptor (3), producing communication between the adaptor (3) and the rear chamber (12) of the barrel (1), the drive nipple (4) carries on its tip (43) which receives the adaptor (3) a spike (44) intended to pierce the fragile wall (34) under the action of the piston propulsion movement.

13 Claims, 2 Drawing Sheets

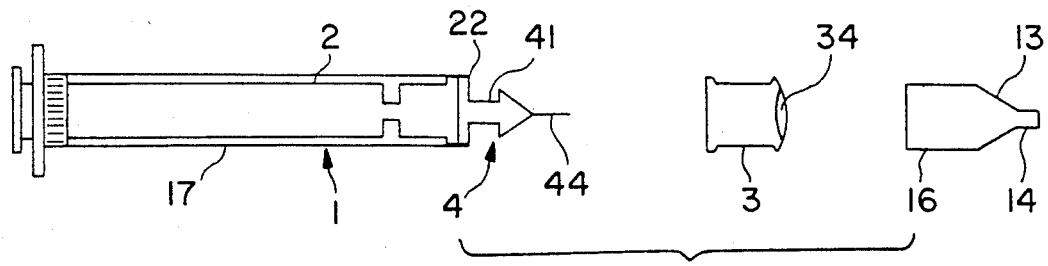
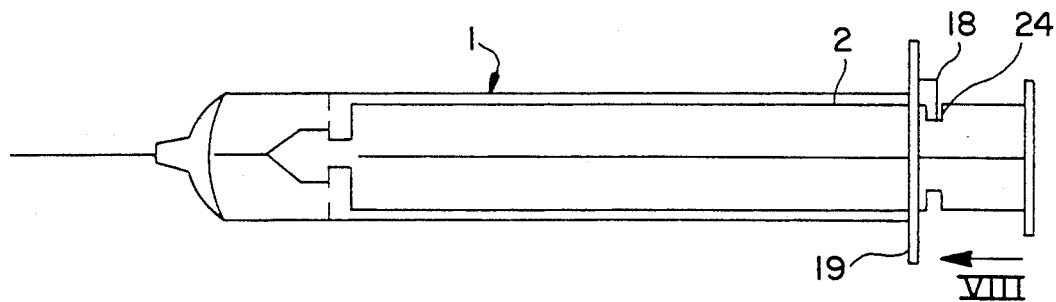
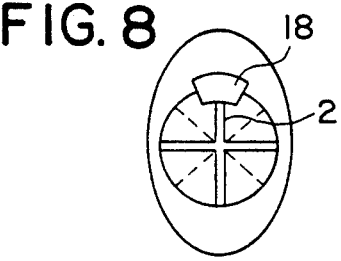
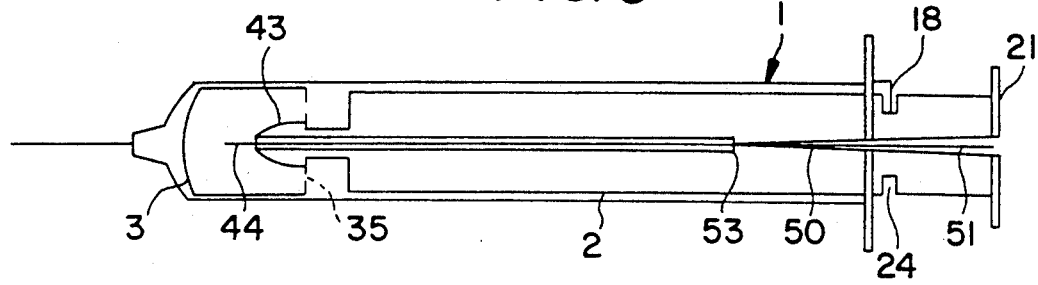

SINGLE-USE HYPODERMIC SYRINGE

This is a continuation of application Ser. No. 07/613,628, filed Nov. 20, 1990 now abandoned.

The present invention relates to a hypodermic syringe intended to be used only once and comprising a barrel receiving a piston fitted with an adaptor in the form of a hollow cylindrical body having a peripheral wall to ensure sealing-tightness in respect of the barrel, a closed front face, a rear face provided with an orifice for fitting the adaptor onto the tip of a piston drive nipple.

Although this syringe, very widely established and of which tens of millions are manufactured and used every year as a so-called 'disposable' syringe, nothing in the structure of this syringe means that it cannot be used after it has been used on a first occasion.

This prior art syringe is regarded as a disposable syringe more than a syringe intended to be used only once because it is produced mainly from synthetic plastics material, is cheap and is unlike the older non-disposable syringes, of which only the needle had to be changed.

Now, with the spread of serious diseases which can be transmitted via the blood, it becomes necessary to provide a syringe which by virtue of its construction cannot be used again.

There is already available a disposable syringe of the type referred to above (U.S. Pat. No. 4,687,467). In this syringe, the needle has a cutting edge which projects to the rear, into the barrel. When the piston reaches the end of its travel during ejection of the fluid, its adaptor becomes impaled on the rear cutting edge of the needle. Thanks to the hollow structure of the drive nipple, the two chambers of the cylinder communicate and this prevents the syringe being used again.

This syringe may likewise be used again if the first user (intentionally or unintentionally) does not completely drain the syringe, that is to say if the user draws in a volume of liquid which exceeds that which has to be injected.

Furthermore, this syringe calls for a special construction of the rear part of the needle and of the adaptor and above all a complicated shape has to be given to the end of the piston, that is to say the drive nipple and its tip.

There is also a completely different type of disposable syringe available (EP A1 0 291 109). This prior art syringe is completely different in structure from conventional syringes because it replaces the sealing-tight adaptor at the end of the piston by a disc fitted with a sleeve in which the piston rod can slide to break through the centre of the disc when the piston rod is propelled (injection phase). Sealing-tightness is provided by the spike which closes the orifice made in the disc. When there is a retracting movement of the piston, the spike is perceived to clear the orifice made in the piston so that the two chambers on either side of the piston are caused to communicate.

However, as the piston rod is provided with a collar which bears on a collar inside the sleeve, at the rear of the piston disc, it is not really possible to produce an effective communication between the two chambers so that it is still possible to fill the syringe again; in other words, the syringe is by no means a single-use syringe.

Furthermore, current manufacturing conditions do not make it possible to produce in an economically viable way a piston disc which is sealing-tight during induction and during delivery.

The object of the present invention is to remedy these drawbacks of the prior art solutions and proposes developing on the basis of conventional syringes a syringe which is truly of the once-only type, while making it possible to benefit from the particularly effective and economic conditions under which prior art syringes are manufactured.

To this end, the invention relates to a syringe of the type mentioned hereinabove, characterised in that:
the front closed face of the adaptor comprises a fragile wall,
the rear face of the adaptor comprises in addition to the orifice at least one other aperture which is situated outside the field of contact of the drive nipple and of the adaptor, producing communication between the adaptor and the rear chamber of the cylinder,
the drive nipple (4) carries on its tip which receives the adaptor a spike intended to pierce the fragile wall under the action of the piston propulsion movement.

The syringe according to the invention is intrinsically a syringe which can be used just once because directly the user exerts any thrust on the piston rod, the spike breaks through the wall of the front face of the adaptor. This consequence is inevitable whatever steps are taken by the user, even one with improper intentions who would like to be able to use the syringe again or use one which had been thrown away.

Other characteristics of the invention are the object of claims 2 to 8.

The rear face of the adaptor likewise has apertures distributed in such a way that they can be occluded by the transverse web of the piston.

According to other characteristics:
the rod of the drive nipple is substantially longer than the thickness of the adaptor so that this latter is displaced between a first position in which its face is against the end web and a second position in which the face is against the transverse face of the conical tip which forms the drive nipple;
the spike pierces the fragile wall in the said first position while sealing-tightness of the adaptor is completed by the occlusion of the apertures by the end web, while the said spike is at a distance from the fragile wall in the said second position, the said adaptor then ensuring communication between the chambers of the cylinder;
stop means prevent the piston being withdrawn outside the barrel;
the piston is rendered fragile by a circumferential groove so that it can be broken;
the barrel is made in two parts which are assembled together;
stop means arrest any displacement of the piston so long as an operating procedure has not been pursued.

The invention will be more clearly understood from reading the ensuing description which is given with reference to the accompanying drawings, in which.

FIG. 6 diagrammatically shows the assembly of the syringe according to the invention;

FIG. 7 is a view of an alternative embodiment of syringe according to the invention;

FIG. 8 is a view according to the arrow VIII in FIG. 7, and

FIG. 9 is a sectional view of the syringe according to a second alternative embodiment.

Figure 1:
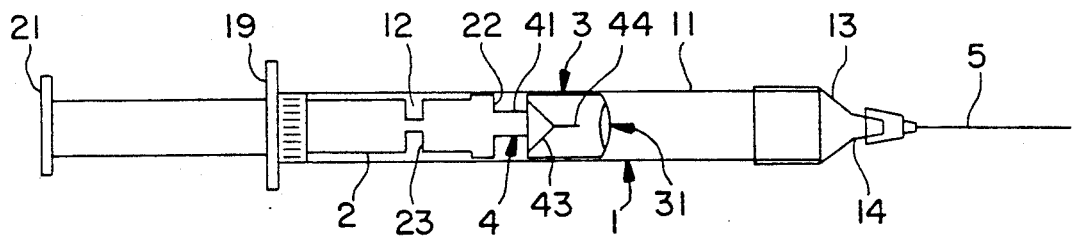
FIG. 1 is a view of a syringe according to the invention.
Figure 2:
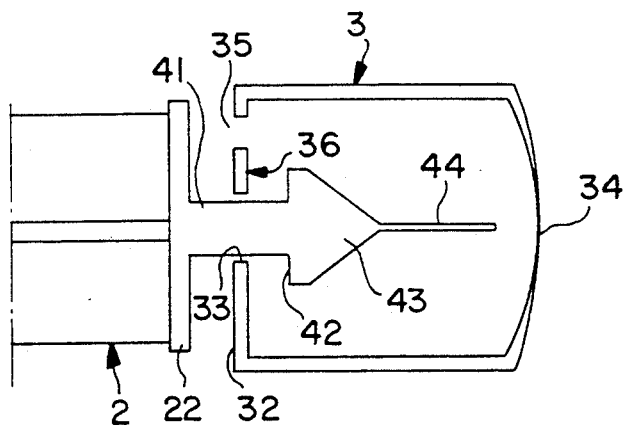
FIG. 2 shows on a larger scale a portion of FIG. 1.

FIG. 2 shows the hypodermic syringe which has a barrel 1, an open end of which is edged by a collar 19; the other end comprises a conical end member 13 which terminates in an open nozzle 14 of small size which is intended to receive the needle 5.

The barrel 1 receives an axially movable piston 2; the piston carries a flat surface 21 which is acted upon by the syringe user, at the end which is outside the barrel; the end which is situated in the barrel 1 comprises a drive nipple 4 by which the piston carries a hollow adaptor 3.

The adaptor 3, constructed from a deformable material, has its outer periphery fitted snugly against the inside wall of the barrel 1 and divides it in sealing-tight fashion into two chambers 11, 12.

According to FIG. 2, the drive nipple 4 of the piston 2 comprises, in succession:

a transverse web 22, a rod 41 extending from the web 22 in the longitudinal axis of the syringe towards the front end of the syringe, at the end of the rod 41, a tip 43 of generally conical or cylindrical-conical form having on its rear face a transverse face 42 and on the front face a spike 44.

The adaptor 3 of deformable material, for example a rubber material, generally takes the form of a hollow cylinder, the front face 31 of which is closed while the rear face 32 comprises an axial aperture 33 of a diameter approximately equal to that of the rod 41 of the drive nipple.

The front closed face 31 of the adaptor 3 is of variable thickness; its central part 34 is of small thickness so that it can be easily torn or pierced. This fragile part 34 is obtained either in a single piece by integrally moulding one thin wall, or by producing an adaptor having an aperture in the central part 34 of the front face and by fitting onto this aperture a wall of reduced thickness which is fragile, being of the disc type and being, for example, welded by ultrasonic or by any other known means.

The face 32 comprises apertures 35, here they are three in number.

Figure 3:
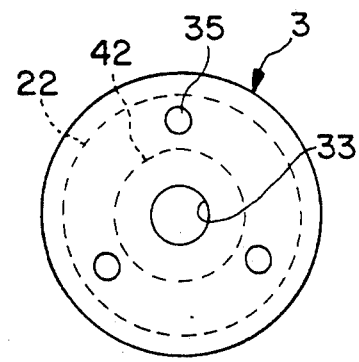
FIG. 3 is a view of the adaptor from the rear.

As FIG. 3 shows, these apertures 35 are circumferentially distributed and are centred on a mean circumference between the disc covered by the web 22 and that covered by the transverse face 42 of the tip 43.

The thickness of the rear wall 36 of the adaptor 3 is substantially less than the length of the rod 41 in order to allow an axial displacement of the adaptor along the rod 41 between the web 22 and the face 42. Thus, for a specific portion of the adaptor in the syringe, the piston is capable of moving freely between two ends of the rod 41.

The syringe is manufactured and marketed with the piston 2 pushed into the cylinder so that the face 31 of the adaptor 3 is close to the bottom 13 of the barrel.

When used for the first time, the piston 2 is pulled in the direction which would tend to cause it to emerge from the barrel 1 in order to draw in the fluid which is to be injected. During this phase, the adaptor 3 has its face 32 bearing against the face 42 of the drive nipple 4.

When the piston is pushed back in the direction of the end 13 of the barrel, there is first of all a displacement of the piston 2 in relation to the adaptor 3 until the piston 2 has its web 22 bearing against the face 32 of the adaptor.

During the course of this relative displacement of the barrel and of the drive nipple in relation to the adaptor 3, the spike 44 which was initially situated at a short distance from the face 31, pierces the fragile portion 34 of the face 31 of the adaptor 3. Furthermore, this piercing is ensured by deformation of the face 31 due to the resistance opposed to it by the fluid when the piston is being propelled.

Upon displacement of the piston 2 towards the bottom of the barrel, the web 22 is in contact with the face 32 of the adaptor and so occludes the apertures 35, the syringe thus functioning as a known type of syringe and expelling through the needle 5 the liquid contained in the chamber 11.

Up to this point, operation of the syringe, at least from the user's point of view, has been the same as that of a prior art type of syringe. However, without the user noticing and without his having to cause it and, furthermore, in a quite interesting manner without his being able to avoid it, the adaptor 3 has been pierced by the spike 44.

In order to ensure sealing-tightness between the web 22 and the face 32, it is necessary for the apertures 35 to be reliably closed. If necessary, it is possible to provide a collar which goes beyond the surface 32 and which is turned towards the web 22; the collar is of a diameter which is sufficient to conceal the apertures 35.

As the syringe cannot again be filled with fluid since the adaptor 3 produces communication between the two chambers 11 and 12, it cannot therefore be used again.

In order to prevent the user withdrawing the piston 2 in order to fill the cylinder 1 again through its open end, locking means are provided in the barrel, on the side of the open end.

Figure 4:
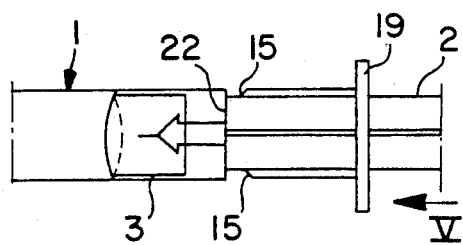
FIG. 4 is a partial view of the open rear end of the barrel.
Figure 5:
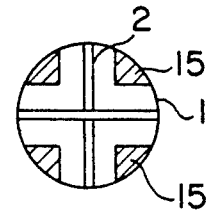
FIG. 5 is a view according to the arrow V in FIG. 4.

As shown in FIGS. 4 and 5, these locking means may take the form of tongues 15 obtained from clefts in the wall of the cylinder 1; these tongues move away from the wall towards the axis of the barrel, moving towards the end of the said barrel.

The tongues 15 are flexible, which allows them to move aside to enter the piston 2 in the barrel and then, when the web 22 is positioned between the said tongues and the end of the barrel, any movement which seeks to move the piston out of the barrel will be arrested by the said web 22 abutting the tongues.

As FIG. 5 shows, the piston 2 having in its moving part a cruciform cross-section, the tongues could be four in number, each being situated in a quadrant which is left free by the piston.

Of course, the stop means could be designed in any other way. By way of example, a bead could be created inside the barrel 1. For this purpose, the collar 19 of the barrel 1 is connected to the end of this latter and has an inner circumference which is greater than the interior of the barrel which is flexible to allow the piston 2 to be forced in when it is placed in position.

The syringe cannot in any way be filled again when it has already been used a first time since the adaptor will no longer provide sealing-tightness in the barrel.

In order even more reliably to prevent the syringe being used again, in addition to the piercing of the adaptor preventing the induction of fluid, it is possible to provide for means of partially destroying the syringe.

For this purpose, the piston 2 comprises at a short distance from the end web 22 a circumferential groove 23 which renders the piston fragile and allows the user to break it after the transfusion. Once the portion of piston 2 emerging from the outside of the barrel is broken, it becomes impossible to remove the remaining portion carrying the adaptor 3 in the direction necessary to draw in fluid.

A method of manufacturing the syringe will be described hereinafter. It is essential to carry out assembly with great care in order not to pierce the fragile wall 34.

In a first embodiment, shown in FIG. 6, the barrel 1 is provide din two parts, one part 16 of short length at the front of the syringe comprising the end member 13 and the nose 14 and the other 17, larger, comprising the cylindrical tube, the rear open end and the collar 19 which surrounds it.

The piston 2 is introduced into the portion 17 until its transverse face 22 is flush with the front end face of the said portion 17 of the barrel 1. The adaptor 2 is then mounted on the drive nipple 4, the length of the spike 44 being such that, at rest, it is sufficiently remote from the fragile wall 34. In order to be certain not to push in the adaptor 3 until it is against the web 22, which would entail the risk of causing the spike 44 to pierce the fragile wall 34, it is possible to fit onto the rod a template which arrests its movement.

It is possible furthermore to provide an adaptor of a length substantially greater than the length of the spike 44 so that the fragile wall 34 remains remote from the spike. Alternatively, it is possible to provide an adaptor of which the diaphragm has at the front an orifice and, after fitment on the drive nipple, a fragile wall 44 may be fitted into this orifice.

Once the adaptor 3 is thus placed in position on the piston 2, the template is removed if it has been used, after which the said adaptor has fitted on it the portion 16 of the barrel which is attached to the portion 17 by any known means such as gluing, ultrasonic welding, etc. . . .

It can be seen that the portion 16 is slightly longer in length than the adaptor 3 so that this latter is close to the end 13 but does not touch it in order not to risk piercing the wall 34 which would then render the syringe useless.

In order not to risk accidental handling of the piston, for example in the direction of the end 13 of the syringe, which would break through the wall 34 before the said syringe is used, stop means 18, 24 are provided such that it is necessary to follow a precise procedure when using the syringe in order to displace the piston 2.

As can be seen in FIGS. 7 and 8, the stop means may consist of a peg 18 rigid with the barrel 1 positioned in a notch 24 in the piston 2. When the piston 2 is in the position shown by solid lines in FIG. 8, it is impossible to move it axially in the barrel. To use the syringe, it is necessary to turn the piston 2 on itself to bring it into the position shown by dotted lines in FIG. 8 so that the peg 18 no longer co-operates with the notch 24.

Preferably, in the embodiment shown, where the piston is in the form of a 'spider', each leg comprises a notch 24 and the peg has a triangular shape at the tip which is slightly less than 90°. Thus, release of the piston is possible only after a considerable rotation of 90° maximum, which avoids accidental unlocking.

The syringe according to the invention is produced using conventional materials already approved by medical authorities without the need for any new materials to be chosen. Particularly, the spike 44 or the needle may be made of synthetic plastics material identical to that of the piston body. Thus it is certain that these materials are suitable for the medical use which it is desired to make of them.

I claim:

1. A disposable hypodermic syringe of the type comprising:
    (a) a syringe barrel (1) having an open end, a cylindrical body, and an opposite end capped by an end member (13) which is adapted to hold a canula needle (5) and to serve as a nozzle between the interior of the barrel and the canula bore of the needle;
    (b) a piston plunger inserted into the open end of the barrel and moveable axially therein, said plunger comprising a piston rod (2) having a handle (21) extending outside the barrel and a piston adaptor (3) attached to the rod end, said adaptor inserted into the barrel to form a slidable seal against the inside wall of the barrel's cylindrical body and form a fluid chamber (11) between said adaptor and said end member;
    said syringe characterized in that it is constructed to be capable of only single use, by the improvement comprising:
    (c) said adapter being a generally hollow body having a cylindrical peripheral wall to seal against the inside wall of the barrel's cylindrical body, a fragile wall (34) closing the front of the adaptor facing toward the barrel's end member, and a generally flat rear wall (32) having an axial aperture (33) and at least one additional aperture (35) into the hollow body;
    (d) a nipple means (4) for operatively attaching the adaptor to the piston rod, said nipple means comprising a generally circular web (22) having one face attached to the piston rod, a rod (41) extending from the opposite face along the longitudinal axis of the web, and a generally conical nipple (43) having its base attached co-axially to the rod and its tapered end terminating in a sharp spike (44);
    (e) said adapter being operably attached to said nipple means by the rod extending through the axial aperture of the adapter such that the rear wall of the adapter may slide along the rod between the circular web and the base of the conical nipple; and
    (f) said adapter and nipple means cooperating to render the syringe capable of only single use by (i) the length of the rod being sufficient to cause the spike to perforate the adapter's fragile front wall when the adapter's rear wall is adjacent to the circular web, but not cause the spike to contact the front wall when the adapter's rear wall is forward of some intermediate position along the rod, and (ii) the circular web having a radius sufficient to cover and seal each said additional aperture when the adapter is adjacent to the web.

2. A syringe as in claim 1, further comprising the adaptor being an integral structure formed from a unitary resilient material.

3. A syringe as in claim 1, further comprising the adaptor being formed by an integral structure of unitary resilient material defining the hollow cylindrical body with an axial orifice in its front wall, and said orifice covered by a disk of fragile material.

4. A syringe as in claim 2, further comprising the piston rod and nipple means being an integral structure formed from a unitary plastic material.

5. A syringe as in claim 3, further comprising the piston rod and nipple means being an integral structure formed from a unitary plastic material.

6. A syringe as in claim 4, further comprising:
 (g) said piston rod being rotatable within the syringe barrel and formed as cruciform web having four narrow blades, each blade having a height dimension sized to conform to the inner radius of the barrel's cylindrical body except for each blade having a short section of lower height at the same position along its length as the other blades, which sections together form a circumferencial notch (24) in the cruciform web; and
 (h) the syringe barrel having at its open end an arcuate flange (18) extending radially inward less than the depth of said notch and extending over an arc of less than 90°;
wherein said notch and flange cooperate to lock the syringe against axial movement of the rod within the barrel when the flange is positioned in the notch, and the syringe can be unlocked by rotating the rod relative to the barrels such that the flange is moved out of the notch.

7. A syringe as in claim 5, further comprising:
 (g) said piston rod being rotatable within the syringe barrel and formed as cruiform web having four narrow blades, each blade having a height dimension sized to conform to the inner radius of the barrel's cylindrical body except for each blade having a short section of lower height at the same position along its length as the other blades, which sections together form a circumferencial notch (24) in the cruciform web; and
 (h) the syringe barrel having at its open end an arcuate flange (18) extending radially inward less than the depth of said notch and extending over an arc of less than 90°;
wherein said notch and flange cooperate to lock the syringe against axial movement of the rod within the barrel when the flange is positioned in the notch, and the syringe can be unlocked by rotating the rod relative to the barrels such that the flange is moved out of the notch.

8. A syringe as in claim 6, further comprising said syringe barrel being constructed of two discrete parts: a first part (17) including the open end and the cylindrical body, and the second part (16) including the end member adapted to hold the canula needle, said second part further being adapted to fit over and be bonded to the first part.

9. A syringe as in claim 7, further comprising said syringe barrel being constructed of two discrete parts: a first part (17) including the open end and the cylindrical body, and the second part (16) including the end member adapted to hold the canula needle, said second part further being adapted to fit over and be bonded to the first part.

10. A syringe as in claim 8, further characterized as being a product which is manufactured from the following unassembled components: first part (17), second part (16), integral piston rod (2) and nipple means (4), and integral adaptor (3); by a process comprising the steps of:
 (a) inserting the integral piston rod and nipple means into the first part until the circular web (22) is flush with the end of the first part opposite the flange (18);
 (b) rotating the rod relative to the first part to engage the flange in the notch (24);
 (c) inserting the nipple through the axial bore of the adapter; and
 (d) fitting the second part (16) over the adapter and the rim of the first part; and
 (e) bonding the second part to the first part.

11. A syringe as in claim 10, manufactured by the process further comprising: placing a template on the rod (41), before inserting the nipple through the axial bore, to prevent the adapter from being placed over the nipple so far that the spike (44) contacts the front wall (34);

12. A syringe as in claim 9, further characterized as being a product which is manufactured from the following unassembled components: first part (17), second part (16), integral piston rod (2) and nipple means (4), adaptor with an axial orifice in its front wall, and a disk of fragile material; by a process comprising the steps of:
 (a) inserting the integral piston rod and nipple means into the first part until the circular web (22) is flush with the end of the first part opposite the flange (18);
 (b) rotating the rod relative to the first part to engage the flange in the notch (24);
 (c) inserting the nipple through the axial bore of the adapter;
 (d) mounting the disk of fragile material over the orifice;
 (e) fitting the second part (16) over the adapter and the rim of the first part; and
 (e) bonding the second part to the first part.

13. A syringe as in claim 12, manufactured by the process further comprising: placing a template on the rod (41), before inserting the nipple through the axial bore, to prevent the adapter from being placed over the nipple so far that the spike (44) contacts the disk.

* * * * *